United States Patent [19]

Bergman et al.

[11] Patent Number: 4,916,124
[45] Date of Patent: Apr. 10, 1990

[54] INDOLOQUINOXALINES WITH SUBSTITUENTS IN 6-POSITION CONTAINING CYCLIC GROUPS AS ANTIVIRAL AGENTS

[75] Inventors: Jan O. E. Bergman, Spånga; Stig G. Akerfeldt, Saltsjö-Duvnäs, both of Sweden

[73] Assignee: Lief Lundblad, Huddinge, Sweden

[21] Appl. No.: 102,146

[22] PCT Filed: Jan. 19, 1987

[86] PCT No.: PCT/SE87/00020
§ 371 Date: Nov. 18, 1987
§ 102(e) Date: Nov. 18, 1987

[87] PCT Pub. No.: WO87/04437
PCT Pub. Date: Jul. 30, 1987

[30] Foreign Application Priority Data

Jan. 21, 1986 [SE] Sweden .............................. 8600261

[51] Int. Cl.$^4$ .................. A61K 31/495; C07D 413/00; C07D 417/00; C07D 403/00
[52] U.S. Cl. .................................... 514/211; 540/599; 540/544; 540/553; 544/96; 544/55; 544/295; 544/343; 514/250; 514/228.8; 514/226.8; 514/212; 514/218
[58] Field of Search ...................... 540/599, 544, 553; 544/96, 55, 295, 343; 514/250, 211, 228.8, 226.8, 212, 218

[56] References Cited

PUBLICATIONS

Chem. Abstracts, vol. 84, (1976) 84:180,166z.
Chem. Abstracts, vol. 66, (1967), No. 1282v.
Chemical Abstracts, vol. 66, (1967), No. 1283c.
Chemical Abstracts, vol. 104, (1986), No. 186375v.

*Primary Examiner*—Lee: Mary C.
*Assistant Examiner*—Robert C. Whittenbaugh
*Attorney, Agent, or Firm*—Browdy and Neimark

[57] ABSTRACT

Novel indoloquinoxalines having substituents in 6-position containing cyclic groups, of the general formula I

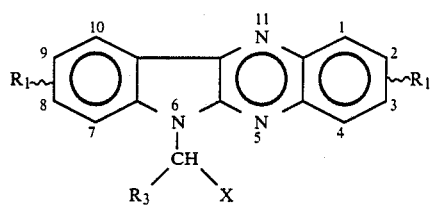

wherein
$R_1$ represents hydrogen or one or several preferably 1 to 4, similar or different substituents in the positions 1–4 and/or 7–10, selected from halogen, lower alkyl-/alkoxy group having not more than 4 carbon atoms, trifluoromethyl group, trichloromethyl group;
X is a group

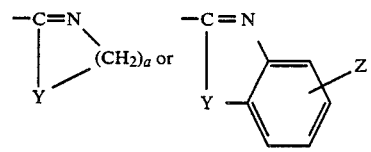

wherein
Y is $CH_2$, NH, O or S and a is 2, 3 or 4 and wherein also the bond —C≡N— can be saturated; Z is alkyl having 1–6 carbon atoms, Cl, Br or $CF_3$ and
$R_3$ represents hydrogen, lower alkyl-/cycloalkyl group having not more than 4 carbon atoms,
and the physiologically acceptable addition products of the compounds with acids and halogen adducts are described. Also methods for preparing said compounds by reaction of a compound of the formula II

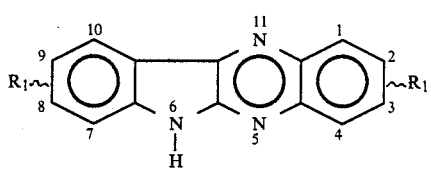

with a reactive compound containing the residue —$CHR_3X$ or by rearranging a compound of the formula III

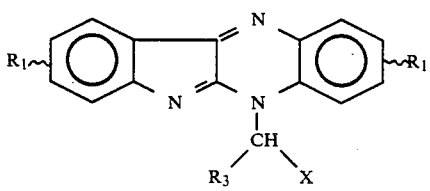

by heating, are described.
The novel indoloquinoxalines have antiviral effect and have effect against cancer.

10 Claims, No Drawings

INDOLOQUINOXALINES WITH SUBSTITUENTS IN 6-POSITION CONTAINING CYCLIC GROUPS AS ANTIVIRAL AGENTS

The present invention relates to novel indoloquinoxalines with substituents in the 6-position containing cyclic groups of the general formula I

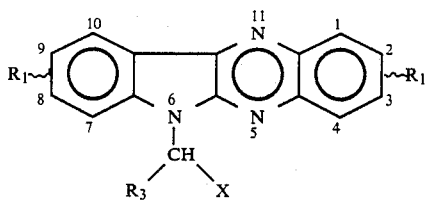

wherein $R_1$ represents hydrogen or one or several, preferably 1 to 4, similar or different substituents in the positions 1–4 and/or 7–10, selected from halogen, lower alkyl-/alkoxy-group having not more than 4 carbon atoms, trifluoromethyl group, trichloromethyl group;

X is a group

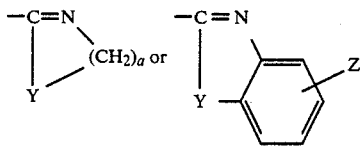

wherein

Y is $CH_2$, NH, O or S and a is 2, 3 or 4 and wherein also the bond —C≡N— can be saturated; Z is alkyl having 1–6 carbon atoms, Cl, Br or $CF_3$ and $R_3$ represents hydrogen, lower alkyl-/cycloalkyl-group having not more than 4 carbon atoms, and the physiologically acceptable addition products of the compounds with acids and halogen adducts, preferably adducts with iodine, iodine monochloride or iodine monobromide.

The novel indoloquinoxalines according to the present invention have a high antiviral effect and several of the compounds show a high anti-cancer effect.

A suitable group of compounds are compounds wherein X is a group

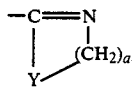

wherein Y=NH, O eller S and a is 2 or 3.

The invention also relates to methods for preparing the novel indoloquinoxalines.

The compounds can be prepared by reaction of 6H-indolo(2,3-b)quinoxalines in the 6-position with a reactive compound containing the residue —$CHR_3X$. Suitable solvents in this context are such as dimethylsulphoxide, dimethylformamide and dimethylacetamide. Alkylation in the 6-position is favoured by low temperature during the reaction. Minor amounts of 5-alkylated 5H-indolo(2,3-b)quinoxalines are formed as byproduct in said alkylation. Previously ethanol has been used as solvent in this type of alkylation, F. Knotz, Sci. Pharm, 39, 20 (1970), F. Knotz, W. Wendelin, Sci. Pharm., 43, 249 (1975). This is unsuitable since with solvents of this type and at the stated temperature a relatively unfavorable isomer ratio is obtained. The 5-alkylated substances have an essentially lower activity.

The 5-alkylated products can a like unalkylated starting material, if any, be removed by chromatography for instance on silica gel with a suitable eluent, for instance methylene chloride/methanol. The starting materials can be prepared by condensation of isatines with o-phenylene diamines. If unsymmetrical o-phenylene diamine is used for this, which is necessary for for instance preparation of 1-, 2-, 3- or 4-mono substituted starting materials, generally isomeric mixtures are obtained which can be difficult to separate. These difficulties can be avoided by preparing 6H-indolo(2,3-b)quinoxalines by condensation of oxindoles with 2-nitroso toluidines as is shown below. R can be hydrogen or a nitrogen containing basic alkyl residue. With aminoalkyl groups as substituent

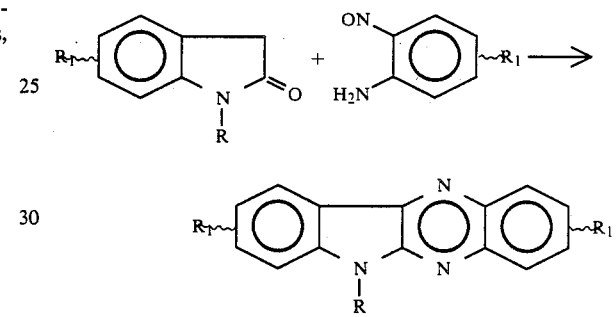

the active compounds can be prepared in one stage.

Another way to avoid the difficulties is to use N-alkylated o-phenylene diamines whereby 5-alkylated 5H-indolo(2,3-b)quinoxalines are obtained. Then the substituent in 5-position can be removed by boiling with hydrogen bromide dissolved in acetic acid.

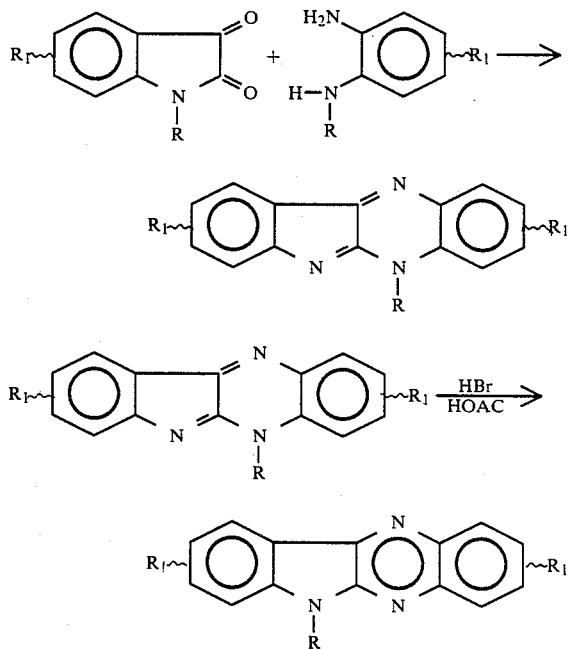

The 5-alkylated 5H-inodlo(2,3-b) quinoxalines can be thermally rearranged to 6-alkylated 6H-indolo(2,3-b)quinoxalines. R can be an aminoalkyl group. Thus, by this rearrangement reaction there is an alternative preparation method for the active compounds.

The anion of indoloquinoxalines was found to be easily alkylated by chloroacetonitrile whereby 6-cyanomethylindoloquinoxalines are obtained which by suitable reduction can be converted to 6-(2-aminoethyl)indoloquinoxalines. Substances of this type also can be prepared as shown below.

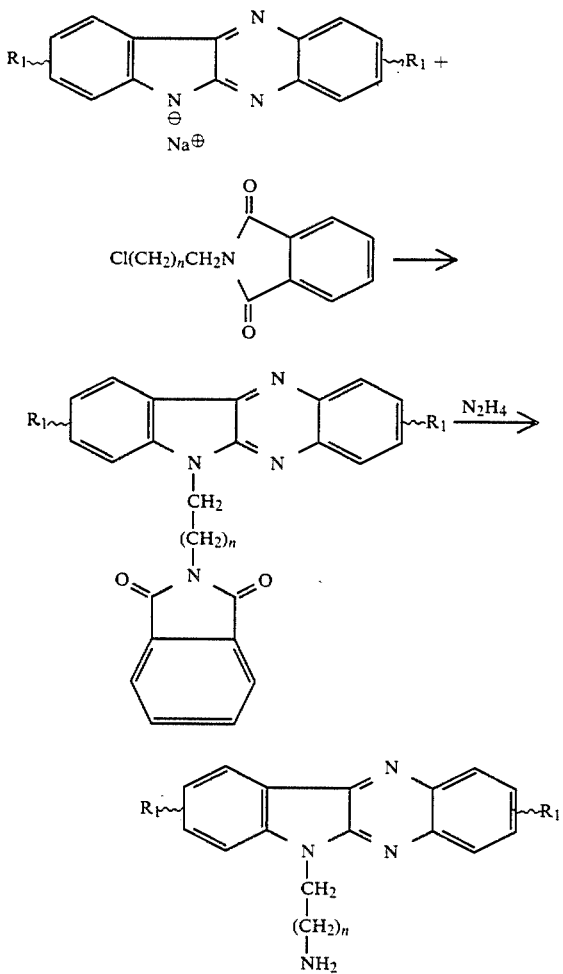

6-cyanomethyl-6H-indolo(2,3-b)quinoxalines are also suitable as starting materials for preparing for instance 6-(Δ-2-thiazolino-2-methyl)-6H-indolo(2,3-b)quinoxalines and 6-(Δ-2-imidazolino-2-methyl)-6H-indolo(2,3-b)quinazolines. When preparing the last mentioned class of substances the addition of sulphur is suitable.

The bases easily can be transformed into physiologically acceptable addition compounds such as hydrochloride, oxalate, tartrate and halogen adducts, preferably adducts with iodine, iodine monochloride or iodine monobromide.

A very interesting group of compounds according to the present invention are the adducts between phosphonoalkanoic acids, such as phosphonoformic acid, phosphonoacetic acid, phosphonopropionic acid, phosphonobutyric acid, phosphonoglycolic acid and its O-acetylderivative, and the indoloquinoxalines of formula I. The last mentioned adducts are interesting since the components per se are antiviral and intervene in different ways in the life cycles of DNA virus. Thus, it is known that phosphonoacetic acid and phosphonoformic acid are active against herpes virus, cf. Applied Microbiology, Volume 26, No. 3, September 1973, Shipkowitz et al, "Suppression of Herpes Simplex Virus Infection by Phosphonoacetic Acid", p. 264–267; Biochemistry, Volume 15, No. 2, 1976, S. Leinbach et al, "Mechanism of Phosphonoacetate Inhibition of Herpesvirus-Induced DNA Polymerase", p. 426–430; Antiviral Research, I (1981), A Larsson and B Öberg, "Selective Inhibition of Herpes virus DNA Synthesis by Foscarnet, p. 55–62; J. gen. Virol., 45, (1979), Bo Sundquist and Bo Öberg "Phosphonoformate Inhibits Reverse Transcriptase", p. 273–281.

Instead of using isolated adducts of the indoloquinoxalines with acids of course directly prepared mixtures of the indoloquinoxalines and the acids can be used.

Indoloquinoxalines without a nitrogen containing basic residue in the 6-position have been described in the literature, cf. Katagiri, K. et al., in Shionogi Kenkyosho Nempo 16 (1966) pp. 52–57. In said article a 6-acetylindoloquinoxaline is described. However, the indoloquinoxalines without any nitrogen containing basic residue in 6-position did not show any effect against virus and/or cancer and the shown inhibition of phages was insignificant.

Knotz (see above) has shown that indoloquinoxalines have effect against certain bacteria which effect however is clearly lower than the effect shown by preparations used today. Knotz has not reported any studies of the effects of the described indoloquinoxalines neither against virus nor against tumor. In view of this the effect shown by the compounds according to the present invention is very unexpected.

The indoloquinoxalines showed powerful inactivation of herpes simplex virus which was studied with a method according to Wahren et al "A novel methiod for determining the sensitivity of herpes simplex virus to antiviral compounds", Journal of Virological Methods, 6 (1983) 141–149, Elsevier Biomedical Press, "Computer-based virus sensitivity assay and neutralization method, applications for herpes viruses", Journal of Virological Methods, 6 (1983) 271–282, Elsevier.

EXAMPLE 1

6-cyanomethyl-6H-indolo(2,3-b)quinoxaline

Indoloquinoxaline (10.95 g) is dissolved in dry dimethyl sulfoxide (150 ml) under nitrogens and sodium hydride (1.3 g) is added with good stirring at 35° C. After completion of hydrogen gas generation (about 30 minutes), chloroacetonitrile (4.0 g) is dropped in with stirring at 20° C. After 1 day at this temperature water (20 ml) is added and crystals formed of pure 6-cyanomethylindoloquinoxaline (8.9 g) are sucked and washed with methanol followed by water. The mother liquor is poured into a large amount of water and the formed precipitate is dried and purified by chromatography on silica gel with methylene chloride/methanol as eluent. In this manner further 3.0 g of 6-cyanomethyl-6H-indolo(2,3-b)quinoxaline are obtained. The total yield thus is 11.9 g, 92%, mp. 231°–232° C.

In the corresponding manner the following compounds are prepared
2,3-dichloro-6-cyanomethyl-6H-indolo(2,3)quinoxaline, mp. 258°–260° C.

2,3-dimethyl-6-cyanomethyl-6H-indolo(2,3-b)quinoxaline, mp. 244°–246° C.
2,3,9-trichloro-6-cyanomethyl-6H-indolo(2,3-b)quinoxaline, mp. 296°–298° C.
2,3-dimethyl-9-chloro-6-cyanomethyl-6H-indolo(2,3-b)quinoxaline, quinoxaline, mp. 286°–288° C.
9-bromo-6-cyanomethyl-6H-indolo(2,3-b)quinoxaline, mp. 246°–247° C.
2,3-dimethyl-9-bromo-6-cyanomethyl-6H-indolo(2,3-b)quinoxaline, mp. 268°–270° C.

EXAMPLE 2

6-(Δ-2-thiazolino-2-methyl)-6H-indolo(2,3-b)quinoxaline 6-cyanomethyl-6H-indolo(2,3-b)quinoxaline (2.58 g) is heated (180° C.) for 45 minutes together with 2-aminoethanethiol (2.5 g). The product formed is recrystallized from dimethylformamide or dimethylsulfoxide and is washed with ethanol and dried. Yield: 2.90 g, 95%, mp. 177°–179° C.

In the corresponding manner the following compounds are prepared
6-(Δ-2-thiazolino-2-methyl)-2,3-dichloro-6H-indolo(2,3-b)quinoxaline, mp. 265°–267° C.
6-(Δ-2-thiazolino-2-methyl)-2,3,9-trichloro-6H-indolo(2,3-b)quinoxaline, mp. 290°–292° C.
6-(Δ-2-thiazolino-2-methyl)-2,3,9-6H-indolo(2,3-b)quinoxaline, mp. 290°–292° C.
6-(Δ-2-thiazolino-2-methyl)-9-bromo-6H-indolo(2,3-b)quinoxaline, mp. 258°–260° C.
6-(Δ-2-thiazolino-2-methyl)-2,3-dimethyl-9-bromo-6H-indolo(2,3-b)quinoxaline, mp. 300°–302° C.

EXAMPLE 3

6-(Δ-2-imidazolino-2-methyl)-6H-indolo(2,3-b)quinoxaline 6-cyanomethyl-6H-indolo(2,3-b)quinoxaline (2.58 g) is heated under reflux (140° C., 3 h) with ethylenediamine (4 ml) in the presence of sulphur (0.2 g) as catalyst. Excess of ethylenediamine is distilled off under reduced pressure and the residue is recrystallized from acetonitrile, 2.09 g, 69%, mp. 218°–220° C.

In the corresponding manner the following compounds are prepared:
6-(Δ-2-imidazolino-2-methyl)-9-bromo-6H-indolo(2,3-b)quinoxaline, mp. 285°–287° C.,
6-(Δ-2-imidazolino-2-methyl)-2,3-dimethyl-9-bromo-6H-indolo(2,3-b)quinoxaline, mp. 298°–300° C.

EXAMPLE 4

6-(Δ-2-imidazolino-2-methyl)-2,3-dimethyl-6H-indolo(2,3-b)quinoxaline 2,3-dimethylindolo(2,3-b)quinoxaline (12.35 g) is dissolved in dry dimethylsulfoxide (200 ml) under nitrogen and with good stirring, and sodium hydride (2.6 g) is added with good stirring at 35° C. After completion of hydrogen gas generation, 2-chloromethyl-4,5-dihydroimidazolhydrochloride (7.75 g) is added in portions at 20° C. After 1 day at this temperature the reaction mixture is poured into water and pH is adjusted to about 10. The base obtained is separated off and dried and recrystallized from methylacetate (with final cooling to −25° C.).

In the corresponding manner the following compound is prepared:
6-(Δ-2-imidazolino-2-methyl)-2,3,9-trichloro-6H-indolo(2,3-b)quinoxaline, mp. 283°–286° C.

EXAMPLE 5

6-(2-aminoethyl)-6H-indolo(2,3-b)quinoxaline.HCl 6-cyanomethyl-6H-indolo(2,3-b)quinoxaline (2.58 g) is heated with reflux under lithium aluminum hydride (0.60 g) in tetrahydrofurane (40 ml) for 6 hours and then water (2 ml) is carefully dropped in. After stirring for 1 hour the solid material is separated away and the residue is concentrated. The residue is dissolved in dry ether and the base is precipitated as hydrochloride by addition of hydrogen chloride 1.40 g, 47%, mp. 280°–282° C.

EXAMPLE 6

6-(3-phthalimidopropyl)-6H-indolo(2,3-b)quinoxaline

Indoloquinoxaline (10.95 g) is dissolved in dry dimethyl sulphoxide (180 ml) under nitrogen and sodium hydride (1.3 g) is added with good stirring at 35° C. After completion of hydrogen gas generation (about 30 minutes) 3-chloro propylphthalimide (11.20 g) is added in portions at 20° C. After 1 day at this temperature the reaction mixture is poured into water. After filtering off and drying, recrystallization from acetonitrile is carried out 15.10 g, 74%, mp. 212°–214° C.

EXAMPLE 7

6-(3-aminopropyl)-6H-indolo(2,3-b)quinoxaline.HCl 6-(3-phthalimidopropyl)-6H-indolo(2,3-b)quinoxaline (4.06 g) is heated under reflux (4 hours) in ethanol (200 ml) wherein hydrazine (0.5 ml) has been dissolved. After heat filtration the filtrate is concentrated and dissolved in dry ether and then hydrogen chloride is added. The precipitate formed is sucked and dried, 3.12 g, 57%, mp. 288°–291° C.

EXAMPLE 8

6-(1,4,5,6-tetrahydropyrimidino-2-methyl)-6H-indolo(2,3-b)quinoxaline 6-cyanomethyl-6H-indolo(2,3-b)quinoxaline (2.58 g) is heated under reflux (160° C., 3 hours) with 1,3-diaminopropane (6 ml) in the presence of sulphur (0.2 g) as catalyst. Excess of 1,3-diaminopropane is distilled offf under reduced pressure and the residue is crystallized from acetonitrile, 2.53 g, 80%, mp. 260°–262° C.

In the corresponding manner the following compound is prepared 6-(1,4,5,6-tetrahydropyrimidino-2-methyl)-2,3-dichloro-6H-indolo(2,3-b)quinoxaline, mp. 302°–304° C.

EXAMPLE 9

6-(3-glutarimidopropyl)-6H-indolo(2,3-b)quinoxaline

Indoloquinoxaline (10.45 g) is dissolved in dry dimethylsulfoxide (80 ml) under nitrogen and sodium hydride (1.3 g) is added with good stirring at 35° C. After completion of hydrogen gas generation, 3-chloropropylglutarimide (9.5 g) is added in portions at 20° C. After 1 day at this temperature the reaction mixture is poured into water. After filtration, drying, recrystallization from acetonitrile is carried out. Yield: 12.0 (64%) mp. 312°–314° C.

In the corresponding manner the following compounds are prepared:
6-(3-glutarimidopropyl)-2-bromo-6H-indolo(2,3-b)quinoxaline, mp. 322°–325° C.

6-(3-glutarimidopropyl)-2,3-dimethyl-9-bromo-6H-indolo(2,3-b)quinoxaline, mp. 340°–342° C.

EXAMPLE 10

6-(3-glutarimidopropyl)-6H-indolo(2,3-b)quinoxaline 6-(3-aminopropyl)-6H-indolo(2,3-b)quinoxaline (2.77 g, 0.01 mole) is heated (3 hours, 170° C.) with glutaric acid anhydride (1.14 g, 0.01 mole) and then the melt is allowed to cool and recrystallization from acetonitrile is carried out. Yield: 3,43, (92%) mp. 312°–314° C.

EXAMPLE 11

6-(3-piperidinopropyl)-6H-indolo(2,3-b)quinoxaline 6-(3-glutarimidopropyl)-6H-indolo(2,3-b)quinoxaline (3.72 g) is heated under reflux with lithium aluminumhydride (0.80 g) in tetrahydrofuran (40 ml) for 6 hours, and then water (2 ml) is dropped thereto carefully. After stirring for 1 hour solid material is separated away and the residue is concentrated. The residue is dissolved in dry ether and the base is precipitated as hydrochloride by addition of hydrogen chloride. Yield: 2.60 g (68%), mp. 262°–266° C.

EXAMPLE 12

6-benzoxazolo-2-methyl-6H-indolo(2,3-b)quinoxaline 6-cyanomethyl-6H-indolo(2,3-b)quinoxaline (2.58 g) and 2-aminophenol (1.09 g) is dissolved in N,N-dimethylacetamide (15 ml) and sulphur (0.2 g) is added. The mixture is heated under reflux (160° C., 24 hours). The product is precipitated by addition of ethanol. Yield: 3.30 g (95%), mp. 242°–244° C.

In the corresponding manner the following compounds are prepared:

6-(benzimidazolo-2-methyl)-6H-indolo(2,3-b)quinoxaline, mp. 228°–230° C., 6-(5,6-dichlorobenzimidazolo-2-methyl)-2,3-dimethyl-9-bromo-6H-indolo(2,3-b)quinoxaline, mp. 288°–290° C., 6-(5-trifluoromethylbenzimidazolo-2-methyl)-2,3-dimethyl-6H-indolo(2,3-b)quinoxaline, mp. 265°–267° C.

6-(benzothiazolo-2-methyl)-6H-indolo(2,3-b)quinoxaline, mp. 270°–272° C., 6-(5,6-dichlorobenzothiazolo-2-methyl)-6H-indolo(2,3-b)quinoxaline, mp. 301°–303° C., 6-(benzothiazolo-2-methyl)-2,3-dimethyl-9-bromo-6H-indolo(2,3-b)quinoxaline, mp. 290°–293° C.

EXAMPLE 13

6-(3-piperidinopropyl)-6H-indolo(2,3-b)quinoxaline-phosphonoacetate 6-(3-piperidinopropyl)-6H-indolo(2,3-b)quinoxaline (344 mg, 0.001 mole) is dissolved in dioxane-ether (15 ml) and a solution of phosphonoacetic acid (140 mg, 0.001 mole) in dioxane-ether (10 ml) is added. After 2 hours at 25° C. the adduct formed is sucked. Yield 434 mg (89%).

We claim:

1. Indoloquinoxalines having substituents in 6-position containing cyclic groups of the formula I

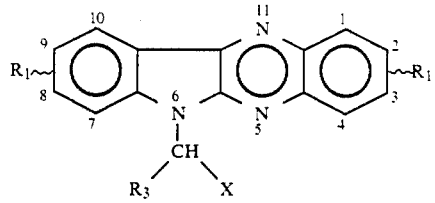

wherein $R_1$ represents hydrogen or one of several, preferably 1 to 4, similar or different substituents in the positions 1–4 and/or 7–10, selected from halogen, lower alkyl-/alkoxy group having not more than 4 carbon atoms, trifluoromethyl group, trichloromethyl group;

X is a group

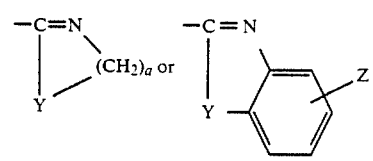

wherein

Y is $CH_2$, NH, O or S and a is 2, 3 or 4 and wherein also the bond $-C=N-$ can be saturated; Z is alkyl having 1–6 carbon atoms, Cl, Br or $CF_3$ and $R_3$ represents hydrogen, lower alkyl-cycloalkyl group having not more than 4 carbon atoms, or a physiologically acceptable addition product of the compounds with a physiologically acceptable acid or a halogen adduct thereof.

2. Indoloquinoxalines according to claim 1, characterized in that X is a group

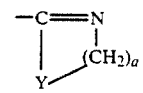

wherein Y=NH, O or S and a is 2 or 3.

3. Indoloquinoxaline according to claim 1, characterized in that it is 6-(Δ-2-thiazolino-2-methyl)-6H-indolo(2,3-b)quinoxaline, 6-(Δ-2-thiazolino-2-methyl)-2,3-dichloro-6H-indolo(2,3-b)quinoxaline, 6-(Δ-2-thiazolino-2-methyl)-2,3,9-trichloro-6H-indolo(2,3-b)quinoxaline, or 6-(Δ-2-imidazolino-2-methyl)-6H-indolo(2,3-b)quinoxaline.

4. Indoloquinoxaline according to claim 1, characterized in that it is an adduct of an indoloquinoxaline of formula I and a phosphonoalkanoic acid.

5. Indoloquinoxaline according to claim 4, characterized in that the phosphonoalkanoic acid is phosphonoformic acid.

6. Indoloquinoxaline according to claim 4, characterized in that the phosphonoalkanoic acid is phosphonoacetic acid.

7. An antiviral agent active against DNA viruses characterized in that it contains as an active component an indoloquinoxaline of the formula

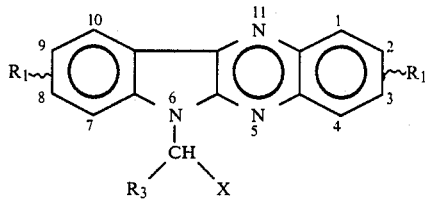

wherein $R_1$ represents hydrogen or one or several preferably 1 to 4, similar or different substituents in the positions 1–4 and/or 7–10, selected from halogen, lower alkyl-/alkoxy group having not more than 4 carbon atoms, trifluoromethyl group, trichloromethyl group;

X is a group

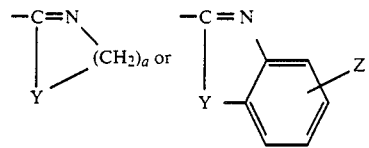

wherein

Y is $CH_2$, NH, O or S and a is 2, 3 or 4 and wherein also the bond —C=N— can be saturated; Z is alkyl having 1–6 carbon atoms, Cl, Br or $CF_3$ and $R_3$ represents hydrogen, lower alkyl-/cycloalkyl group having not more than 4 carbon atoms, or physiologically acceptable addition products of the compounds with a physiologically acceptable acid or a halogen adduct thereof in a pharmaceutically acceptable carrier.

8. An antiviral agent according to claim 7 active against DNA-virus characterized in that it consists of an adduct of an indoloquinoxaline of the formula I and a phosphonoalkanoic acid.

9. An antiviral agent according to claim 8, characterized in that the phosphonoalkanoic acid is phosphonoformic acid.

10. An antiviral agent according to claim 8, characterized in that the phosphonoalkanoic acid is phosphonoacetic acid.

* * * * *